United States Patent
Martin et al.

(10) Patent No.: US 6,800,770 B2
(45) Date of Patent: Oct. 5, 2004

(54) ANTI-SPASTICITY OF AN EICOSANOID ANALOG

(75) Inventors: Billy Martin, Richmond, VA (US); Raj K. Razdan, Gloucester, MA (US); Anu Mahadevan, Woburn, MA (US); David Baker, London (GB)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 10/346,164

(22) Filed: Jan. 17, 2003

(65) Prior Publication Data

US 2004/0002541 A1 Jan. 1, 2004

Related U.S. Application Data

(63) Continuation-in-part of application No. 10/170,204, filed on Jun. 13, 2002, now abandoned.
(60) Provisional application No. 60/348,676, filed on Jan. 17, 2002.

(51) Int. Cl.$^7$ .................. C07C 233/05; A61K 31/16
(52) U.S. Cl. .................. 554/51; 554/54; 554/61; 558/414; 514/509; 514/521; 514/627
(58) Field of Search .................. 554/51, 54, 61; 558/414; 514/509, 521, 627

(56) References Cited

PUBLICATIONS

Marzo et al, Journal of Pharmacology and Experimental Therapeutics, vol. 300, Issue 3, Mar. 2002, pp. 984–991.*

* cited by examiner

*Primary Examiner*—Shailendra Kumar
(74) *Attorney, Agent, or Firm*—Whitham, Curtis & Christofferson, P.C.

(57) ABSTRACT

The invention compounds and methods for the treatment of motor disorders. In particular, the invention provides eicosanoid analogs which are effective in ameliorating motor disorders such as spasticity caused by multiple sclerosis (MS).

18 Claims, 6 Drawing Sheets

O-2093

O-2247

O-2248

ANTI-SPASTICITY OF AN EICOSANOID ANALOG

CROSS-REFERENCE TO RELATED APPLICATIONS

This application claims priority to U.S. Patent Provisional Patent Application Ser. No. 60/348,676, filed Jan. 17, 2002, and claims priority to and is a continuation-in-part of U.S. patent application Ser. No. 10/170,204, filed Jun. 13, 2002 now abandoned. The complete contents of the aforementioned patent applications is hereby incorporated by reference.

This invention was made using funds from grants from the National Institutes of Health having grant numbers NIH DA 09789 and DA-08904 and the Multiple Sclerosis Society of Great Britain and Northern Ireland. The U.S. government may have certain rights in this invention.

BACKGROUND OF THE INVENTION

1. Field of the Invention

The invention generally relates to the treatment of motor disorders. In particular, the invention provides an eicosanoid analog which is effective in ameliorating motor disorders such as spasticity caused by multiple sclerosis (MS).

2. Background of the Invention

Numerous pathological diseases and conditions exist which can severely impair the motor function of afflicted persons. Examples include central nervous system (CNS) disorders such as multiple sclerosis (MS), Huntington's Chorea, amyotrophic lateral sclerosis, and Parkinson's Disease, and acute brain and/or spinal cord injury due to stroke, head or spinal cord trauma, and cerebral palsy. For persons suffering from such diseases or conditions, the consequent inability to control or direct motor function (e.g. spasticity) often severely attenuates the individual's self-care ability and has a huge negative impact on mobility and quality of life. In many cases, other symptoms such as pain and bladder instability also occur.

Cannabinoids are known to display anti-spastic activity by acting at cannabinoid receptors such as the $CB_1$ receptor. However, potential problems and disadvantages associated with utilizing compounds which act as therapeutic agents in this manner are unwanted psychoactive effects, such as euphoria, paranoia, sedation, and psychosis. Further, some cannabinoids such as arvanil and methanandamide display anti-spasticity effects but have the drawbacks that they bind to $CB_1$ and so may induce such side effects, and may also induce irritancy due to stimulation of the vanilloid receptor.

There is thus an ongoing need to develop new, effective therapeutic agents and methods of treatment for motor disorders which are free from these undesirable side effects.

SUMMARY OF THE INVENTION

The present invention provides a novel compound for the treatment of motor disorders such as spasticity associated with multiple sclerosis, and methods for the treatment of patients with such motor disorders. The compound, O-2093, and related derivatives, display excellent anti-spasticity activity. However, O-2093 does not interact significantly with cannabinoid or vanilloid receptors, and thus does not elicit the undesirable side effects associated with activation of those receptors.

The invention thus provides a novel compound having the structural formula

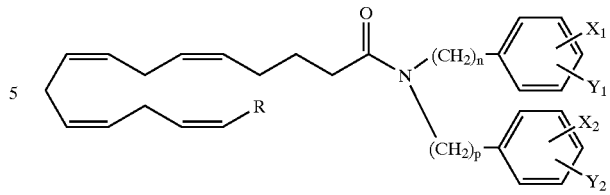

in which the value of n ranges from 0 to about 5, the value of p ranges from 0 to about 5, and n and p may be the same or different; $X_1$=H, alkyl, Cl, Br, I, F, OH, $OCH_3$, or O-alkyl; $X_2$=H, alkyl, Cl, Br, I, F, OH, $OCH_3$, or O-alkyl; $Y_1$=H, alkyl, Cl, Br, I, F, OH, $OCH_3$, or O-alkyl; $Y_2$=H, alkyl, Cl, Br, I, F, OH, $OCH_3$, or O-alkyl; and $X_1$, $X_2$, $Y_1$ and $Y_2$ can be the same or different in any combination; and

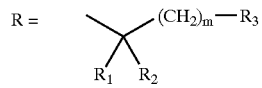

wherein the value of m ranges from 1 to about 7; $R_1$=$R_2$ and may be H or alkyl; and $R_3$=OH, Cl, Br, I, CN, ONO, $ONO_2$, $NO_2$, H, or $CH_3$.

In preferred embodiments of the invention, the compound is one in which:
1) $X_1$ and $X_2$ are Cl; $Y_1$ and $Y_2$ are OH; n and p are 1; $R_1$ and $R_2$ are H; m=3; $CH_3$; or
2) $X_1$ is H and $X_2$ is Cl; $Y_1$ and $Y_2$ are Cl; n and p are 1; $R_1$ and $R_2$ are H; m=3; and $R_3$=$Ch_3$; or
3) $X_1$ is H and $X_2$ is Cl; $Y_1$ and $Y_2$ are Cl; n is 1 and p is 0; $R_1$ and $R_2$ are H; m=3; and $R_3$=$CH_3$.

The invention further provides a method of treating motor disorders in a patient in need thereof. The method includes the step of administering to the patient a sufficient amount of a pure or salt form of a compound having the structural formula

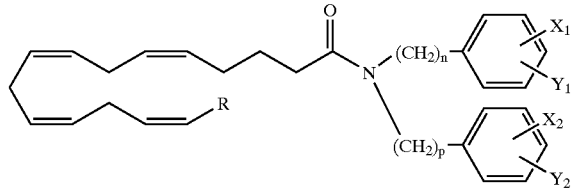

in which the value of n ranges from 0 to about 5, the value of p ranges from 0 to about 5, and n and p may be the same or different; $X_1$=H, alkyl, Cl, Br, I, F, OH, $OCH_3$, or O-alkyl; $X_2$=H, alkyl, Cl, Br, I, F, OH, $OCH_3$, or O-alkyl; $Y_1$=H, alkyl, Cl, Br, I, F, OH, $OCH_3$, or O-alkyl; $Y_2$=H, alkyl, Cl, Br, I, F, OH, $OCH_3$, or O-alkyl; and $X_1$, $X_2$, $Y_1$ and $Y_2$ can be the same or different in any combination; and

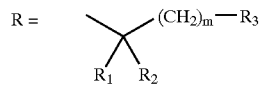

wherein the value of m ranges from 1 to about 7; $R_1$=$R_2$ and may be H or alkyl; and $R_3$=OH, Cl, Br, I, CN, ONO, $ONO_2$, $NO_2$, H, or $CH_3$.

In preferred embodiments of the invention, the compound is one in which:
1) $X_1$ and $X_2$ are Cl; $Y_1$ and $Y_2$ are OH; n and p are 1; $R_1$ and $R_2$ are H; m=3; and $R_3$=$CH_3$; or 2) $X_1$ is H and $X_2$ is Cl; $Y_1$ and $Y_2$ are Cl; n and p are 1; $R_1$ and $R_2$ are H; m=3; and $R_3$=$CH_3$; or 3) $X_1$ is H and $X_2$ is Cl; $Y_1$ and $Y_2$ are Cl; n is 1 and p is 0; $R_1$ and $R_2$ are H; m=3; and $R_3$=$CH_3$.

Administration of the compound may be carried out by any of several suitable known means, including but not limited to intraperitoneal, subcutaneous, oral, intramuscular, and intravenous.

The motor disorder that is treated by the methods of the invention may result from any of several disorders including multiple sclerosis, spinal cord injury, Huntington's disease and Parkinson's disease. The motor disorder may be, for example, spasticity, gait abnormality, or ataxia.

The invention further provides a method for the treatment of spasticity in a patient in need thereof. The method includes the step of administering to the patient a sufficient amount of a compound having the structural formula

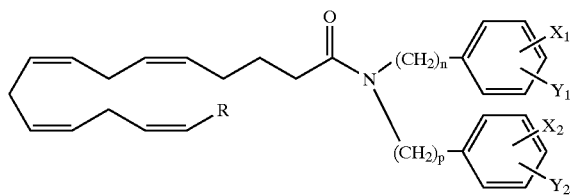

in which the value of n ranges from 0 to about 5, the value of p ranges from 0 to about 5, and n and p may be the same or different; $X_1$=H, alkyl, Cl, Br, I, F, OH, $OCH_3$, or O-alkyl; $X_2$=H, alkyl, Cl, Br, I, F, OH, $OCH_3$, or O-alkyl; $Y_1$=H, alkyl, Cl, Br, I, F, OH, $OCH_3$, or O-alkyl; $Y_2$=H, alkyl, Cl, Br, I, F, OH, $OCH_3$, or O-alkyl; and $X_1$, $X_2$, $Y_1$ and $Y_2$ can be the same or different in any combination; and

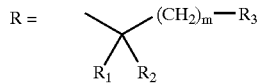

wherein the value of m ranges from 1 to about 7; $R_1$=$R_2$ and may be H or alkyl; and $R_3$=OH, Cl, Br, I, CN, ONO, $ONO_2$, $NO_2$, H, or $CH_3$.

In preferred embodiments of the invention, the compound in one in which:

1) $X_1$ and $X_2$ are Cl; $Y_1$ and $Y_2$ are OH; n and p are 1; $R_1$ and $R_2$ are H; m=3; and $R_3$=$CH_3$; or 2) $X_1$ is H and $X_2$ is Cl; $Y_1$ and $Y_2$ are Cl; n and p are 1; $R_1$ and $R_2$ are H; m=3; and $R_3$=$CH_3$; or 3) $X_1$ is H and $X_2$ is Cl; $Y_1$ and $Y_2$ are Cl; n is 1 and p is 0; $R_1$ and $R_2$ are H; m=3: and $R_3$=$CH_3$.

In the method, the step of administering may be carried out by any of several suitable means such as intraperitoneal, subcutaneous, oral, intramuscular, and intravenous.

The invention further provides a composition comprising,

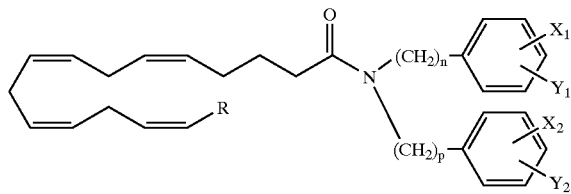

in which the value of n ranges from 0 to about 5, the value of p ranges from 0 to about 5, and n and p may be the same or different; $X_1$=H, alkyl, Cl, Br, I, F, OH, $OCH_3$, or O-alkyl; $X_2$=H, alkyl, Cl, Br, I, F, OH, $OCH_3$, or O-alkyl; $Y_1$=H, alkyl, Cl, Br, I, F, OH, $OCH_3$, or O-alkyl; $Y_2$=H, alkyl, Cl, Br, I, F, OH, $OCH_3$, or O-alkyl; and $X_1$, $X_2$, $Y_1$ and $Y_2$ can be the same or different in any combination; and

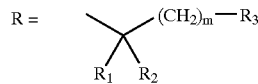

wherein the value of m ranges from 1 to about 7; $R_1$=$R_2$ and may be H or alkyl; and $R_3$=OH, Cl, Br, I, CN, ONO, $ONO_2$, $NO_2$, H, or $CH_3$;

and a carrier in which the compound is dissolved or dispersed. The compound may be present in the carrier in salt form.

DETAILED DESCRIPTION OF THE PREFERRED EMBODIMENTS OF THE INVENTION

Figure 1A:
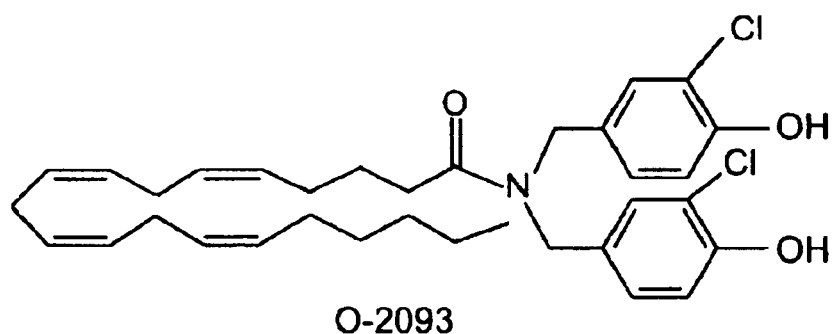
FIGS. 1A, B and C. Chemical structure of the eicosanoid analogs A, N, N-di-3-chloro-4-hydroxybenzylarachadonamide, (O-2093); B, Eicosa-5,8,11,14-tetraenoic acid (4-chloro-benzyl)-(2,4-dichloro-benzyl)amide (O-2247); and C, Eicosa-5,8,11,14-tetraenoic acid (4-chloro-benzyl)-(2,4-dichloro-phenyl)amide (O-2248).
Figure 1B:
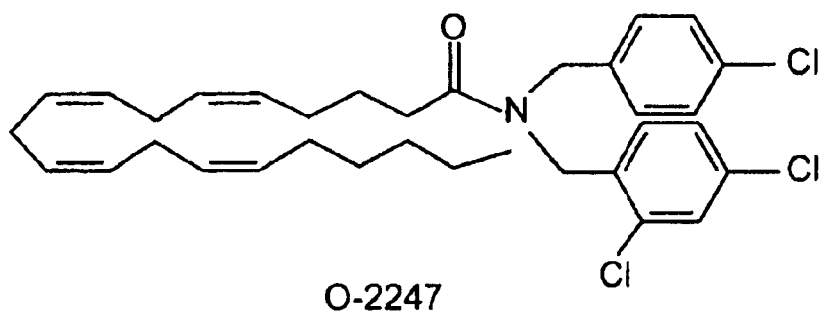
Figure 1C:
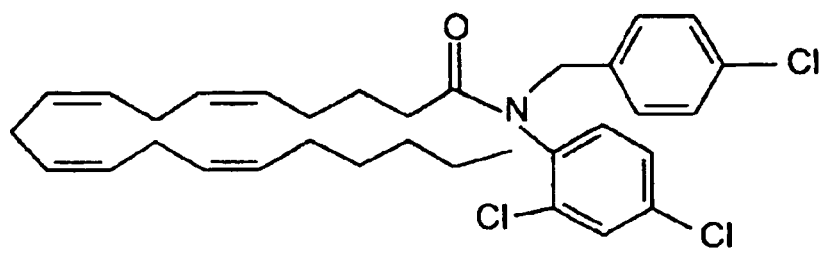
Figure 2A:
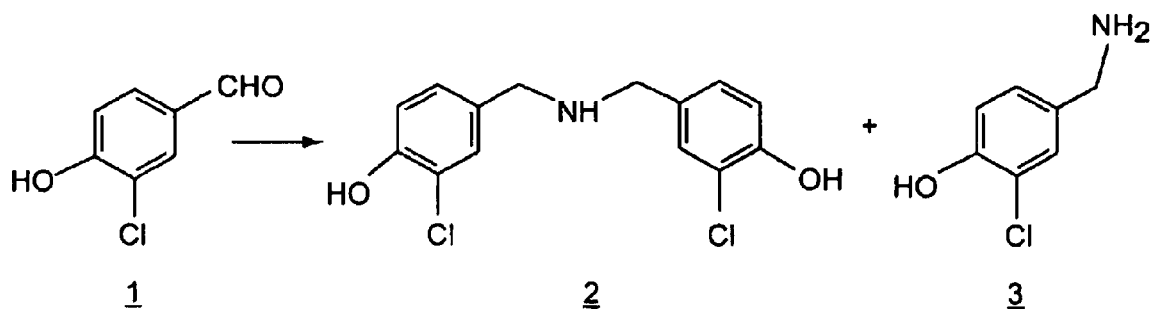
FIGS. 2A, B and C. Synthesis scheme for A, O-2093; B, O-2247; and C, O-2248.
Figure 2A:
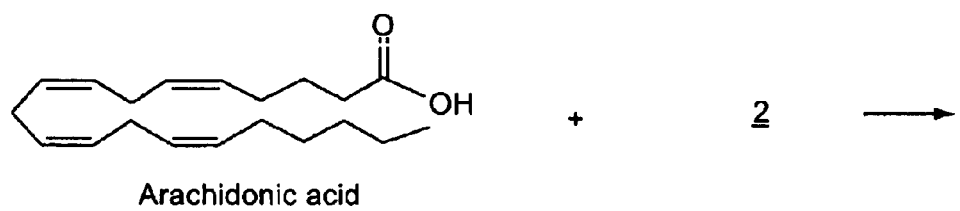
Figure 2A:
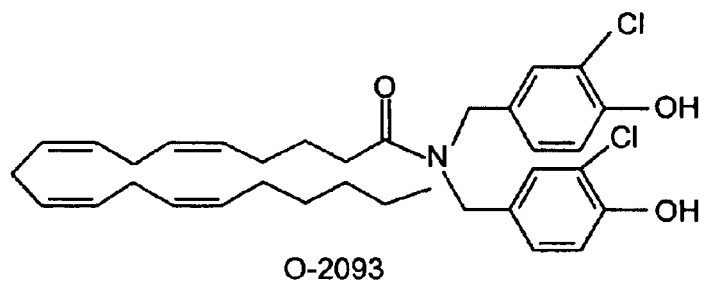
Figure 2B:
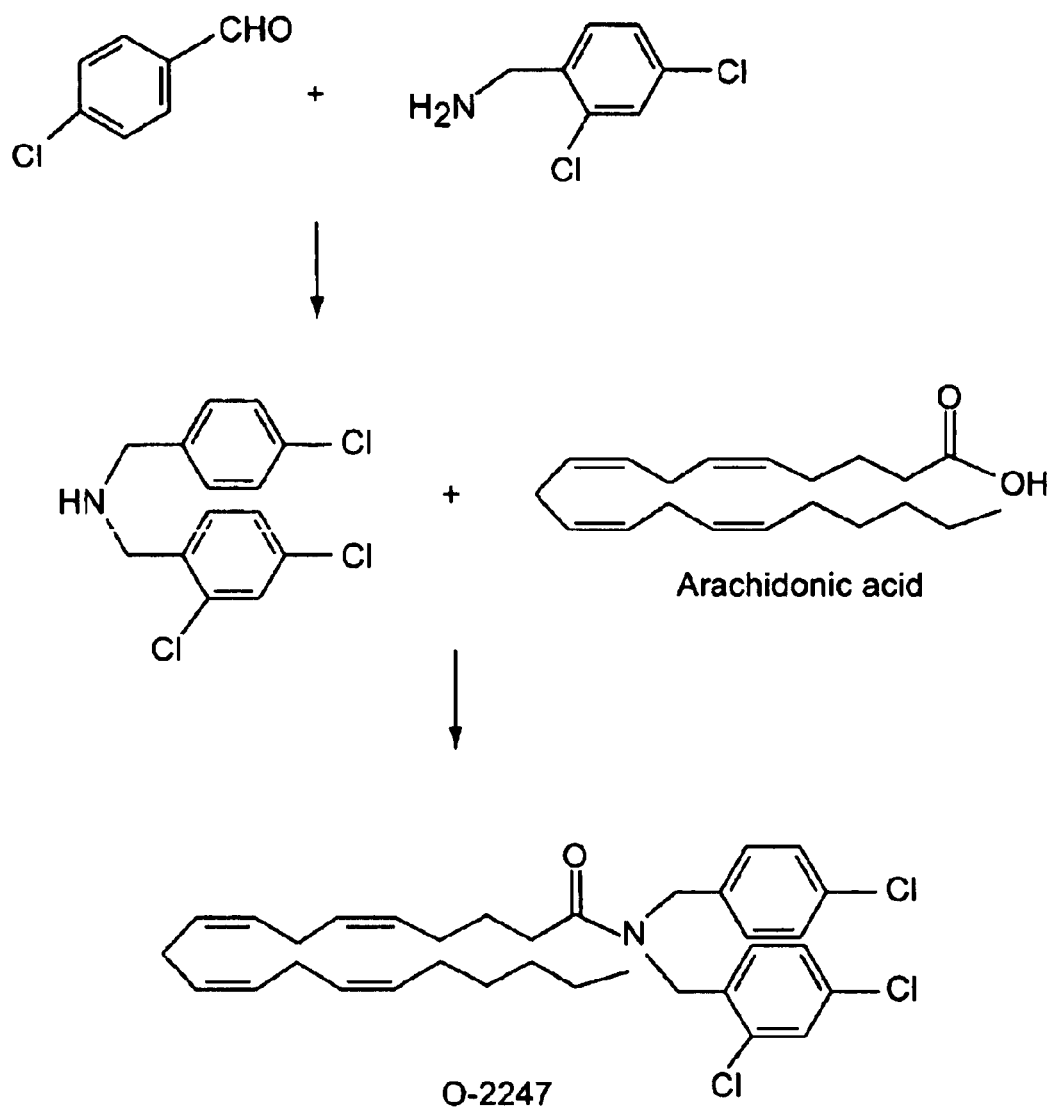
Figure 2C:
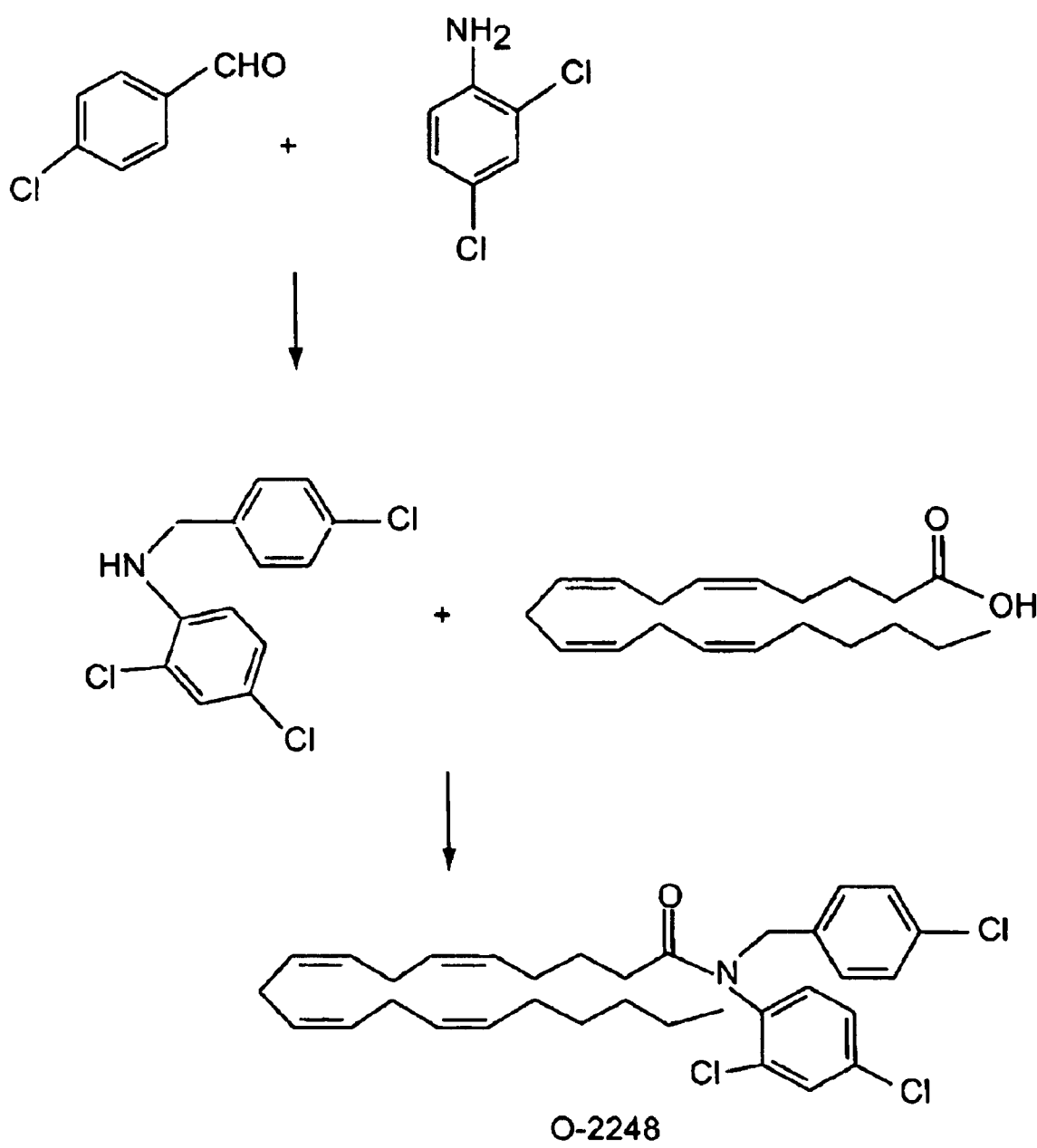

The present invention provides an eicosanoid analog, N, N-di-3-chloro-4-hydroxybenzylarachadonamide, denominated "O-2093", and various derivatives of O-2093 such as O-2247 and O-2248 (see FIG. 1). The compounds are useful in the treatment of motor impairments or dysfunctions, for example, spasticity associated with diseases such as multiple sclerosis (MS). The compounds exhibit little or no affinity for CB1 and vanilloid receptors (see Example 2 below) and so do not elicit the untoward side effects associated with cannabinoid-based anti-spasticity agents.

O-2093 may be synthesized, for example, from a suitable amine precursor which may be in turn formed as a by-product during the reductive amination of 3-chloro-4-hydroxybenzaldehyde. The synthesis of O-2093 and two exemplary derivatives is described in detail in Example 1 below, and is depicted in the synthesis scheme shown in FIG. 2.

Those of skill in the art will recognize that other compounds that are closely related to O-2093 (i.e. derivatives of O-2093) may also be used in the practice of the present invention. A depiction of a generic compound for use in the present invention is given below:

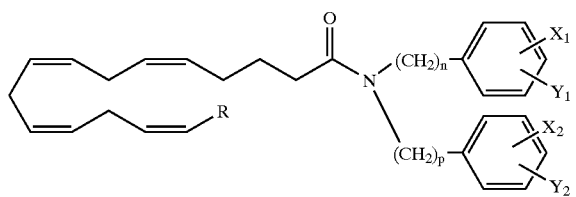

In the compound, n ranges from 0 to about 5, and p ranges from 0 to about 5, and n and p may be the same or different; $X_1$=H, alkyl, Cl, Br, I, F, OH, $OCH_3$, or O-alkyl; $X_2$=H, alkyl, Cl, Br, I, F, OH, $OCH_3$, or O-alkyl; $Y_1$=H, alkyl, Cl, Br, I, F, OH, $OCH_3$, or O-alkyl; $Y_2$=H, alkyl, Cl, Br, I, F, OH, $OCH_3$, or O-alkyl; and $X_1$, $X_2$, $Y_1$ and $Y_2$ can be the same or different in any combination; and

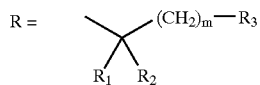

where m ranges from 1 to about 7; $R_1$=$R_2$=H, or alkyl; and $R_3$=OH, Cl, Br, I, CN, ONO, $ONO_2$, $NO_2$, H, or $CH_3$.

In preferred embodiments of the invention,

1) $X_1$ and $X_2$ are Cl; $Y_1$ and $Y_2$ are OH; n and p are 1; $R_1$ and $R_2$ are H; m=3 and $R_3$=$CH_3$; i.e. the compound is O-2093; or 2) $X_1$ is H and $X_2$ is Cl; $Y_1$ and $Y_2$ are Cl; n and p are 1; $R_1$ and $R_2$ are H; m=3 and $R_3CH_3$xi.e. the compound is O-2247; and 3) $X_1$ is H and $X_2$ is Cl; $Y_1$ and $Y_2$ are Cl; n is 1 and p is 0; $R_1$ and $R_2$ are H; m=3 and $R_3$=$CH_3$; i.e. the compound is O-2248.

Those of skill in the art will recognize that a variety of motor disorders can be tr administration of the compounds of the present invention. By "motor disorders" we mean diseases affecting normal motor function, e.g. control of muscle function. Examples of such motor disorders include those due to central nervous system (CNS) disorders such as multiple sclerosis (MS), Huntington's Chorea, amyotrophic lateral sclerosis, and Parkinson's Disease, and acute brain and/or spinal cord injury due to stroke, head or spinal cord trauma, cerebral palsy, anoxic brain damage, and motor deficits due to metabolic disorders such as adrenoleukodystrophy and phenylketonuria.

In particular, one type of motor disorder that may be treated is spasticity, particularly that associated with multiple sclerosis. By "spasticity" we mean a condition typically characterized by stiff or rigid muscles and exaggerated deep tendon reflexes that interferes with muscular activity, gait, movement, or speech. Spasticity generally results from damage to the motor area of the brain (the portion of the cerebral cortex that controls voluntary movement) and to any portion of the subcortical white matter (nerves traveling from brain to spinal cord). Spasticity is generally recognized to be a velocity-dependent increase in resistance to passive movement of a limb in which increased tone and resistance to movement develops in limb or trunk muscles because of damage in the central nervous system.

Implementation of the claimed invention will generally involve identifying patients suffering from motor disorders and administering the compounds of the present invention in an acceptable form by an appropriate route. The exact dosage to be administered may vary depending on the age, gender, weight and overall health status of the individual patient, as well as the precise etiology of the disease. Optimal dosages are typically determined in Phase I clinical trials. However, in general for administration in mammals (e.g. humans), dosages in the range of from about 0.1 to about 30 mg of compound per kg of body weight per 24 hr., and more preferably about 0.1 to about 10 mg of compound per kg of body weight per 24 hr., are effective.

Administration can be oral or parenteral, including intravenously, intramuscularly, subcutaneously, etc., or by other routes (e.g. transdermal, sublingual, aerosol, etc.).

The compounds can be administered in the pure form or in a pharmaceutically acceptable formulation including suitable elixirs, binders, and the like (generally referred to a "carriers") or as pharmaceutically acceptable salts (e.g. ammonium) or other complexes. It should be understood that the pharmaceutically acceptable formulations and salts include liquid and solid materials conventionally utilized to prepare both injectable dosage forms and solid dosage forms such as tablets and capsules and aerosolized dosage forms. Water may be used as the carrier or the preparation of injectable compositions which may also include conventional buffers and agents to render the injectable composition isotonic. Other potential additives include: colorants; surfactants (TWEEN, oleic acid, etc.); and binders or encapsulants (lactose, liposomes, etc). Solid diluents and excipients include lactose, starch, conventional disintergrating agents, coatings and the like. Preservatives such as methyl paraben or benzalkium chloride may also be used. Depending on the formulation, it is expected that the active composition will consist of about 1% to about 99% of the composition and the vehicular "carrier" will constitute about 1% to about 99% of the composition. The pharmaceutical compositions of the present invention may include any suitable pharmaceutically acceptable additives or adjuncts to the extent that they do not hinder or interfere with the therapeutic effect of the active compound.

The administration of the compounds of the present invention can be intermittent, or at a gradual or continuous, constant or controlled rate to a patient. In addition, the time of day and the number of times per day that the pharmaceutical formulation is administered may vary are and best determined by a skilled practitioner such as a physician. Further, the effective dose can vary depending upon factors such as the mode of delivery, gender, age, and other conditions of the patient, as well as the extent or progression of the disease.

EXAMPLES

Example 1

Synthesis of O-2093 (N, N-Di-3-chloro-4-hydroxybenzylarachadonamide) and Related Eicosanoids, O-2247 and O-2248

3-Chloro-4-hydroxybenzylamine and di-(3-chloro-4-hydroxybenzyl)amine. To a stirred suspension of 1.50 g (9.58 mmol) 3-chloro-4-hydroxybenzaldehyde, 20 g ammonium acetate (20 eq), and 30 g 3 Å molecular sieves in 150 mL methanol under nitrogen, was added 903 mg (1.5 eq) sodium cyanoborohydride and the reaction stirred overnight. The solvent was removed under vacuum and the solid residue dissolved in 100 mL water. The solution was saturated with sodium carbonate, then sodium chloride, and extracted with 2×150 mL ethyl acetate. The aqueous phase was subjected to continuous liquid/liquid extraction with ethyl acetate for 7 d. The combined organic phases were plated on 6 g silica and purified by flash chromatography on 86 g silica, eluting with ethyl acetate, then 9 ethyl acetate/1 methanol, then 9 ethyl acetate/1 methanol saturated with anhydrous ammonia. This gave 217 mg (14%) of the primary amine along with 460 mg (32%) of the secondary amine, di-(3-chloro-4-hydroxybenzyl)amine, as white solids.

N,N-Di-3-chloro-4-hydroxybenzylarachadonamide (O-2093). To 212 mg (0.696 mmol) of arachadonic acid in 700 µL ahydrous benzene in a flame dried round bottom flask under nitrogen at 0° C. was added dropwise 121 µL oxalyl chloride (2 eq), followed by 1 drop anhydrous DMF. Copious gas evolved, and the reaction was stirred overnight at room temperature. The solvent was removed under vacuum and the residual oxalyl chloride removed by stripping with 3 mL anhydrous benzene then 1 mL anhydrous methylene chloride. The acid chloride was dissolved in 2 mL anhydrous methylene chloride and cannulated dropwise into 219 mg of di-(3-chloro-4-hydroxybenzyl)amine (1.1 eq) in 4 mL anhydrous THF at 0° C. under nitrogen. A white precipitate formed and the reaction was stirred 3 h at room temperature. The solids were removed by vacuum filtration and washed with 3×10 mL chloroform. 20 mL THF was added to the combined filtrate which was washed with 50 mL each 1 N HCl, saturated aqueous sodium bicarbonate, and brine, dried on sodium sulfate, and the solvent removed under vacuum. The crude product was plated on 1 g silica and purified by flash chromatography on 29 g silica, eluting with 49 hexanes/1 ethyl ether, then 4 hexanes/1 ethyl ether, then 2 hexanes/1 ethyl ether, then 1 hexanes/1 ethyl ether. This gave 162 mg (75% based on the amine) of the product as an off white wax.; $^1$H NMR (CDCl$_3$) δ7.0 (m, 6H), 6.1 (br s, 2H), 5.34 (m, 8H), 4.47 (d, 2H), 4.34 (d, 2H), 2.80 (m, 6H), 2.42 (t, 2H), 2.05 (m, 4H), 1.82 (m, 2H), 1.27 (m, 6H), 0.88 (t, 3H); Anal. Calc for $C_{34}H_{43}NO_3Cl_2$: C, 69.85, H, 7.41, N, 2.40, Cl, 12.13. Found: C, 69.96, H, 7.52, N, 2.31, Cl, 12.12.

Eicosa-5,8,11,14-tetraenoic acid (4-chloro-benzyl)-(2,4-dichloro-benzyl)amide (O-2247). 4-Chlorobenzaldehyde (2 g, 14.23 mmol) was dissolved in 1,2-dichloroethane (65 mL) and acetic acid (0.82 mL, 14.23 mmol). 2,4-dichlorobenzylamine (2.8 g, 15.65 mmol) was added followed by sodium triacetoxyborohydride (4.8 g, 22.79 mmol). The mixture was stirred at 25° C. for two days. Separated layers with saturated NaHCO$_3$ and EtOAc. The aqueous layer was extracted further with EtOAc. The combined organic layers were washed with brine, dried (MgSO$_4$) and solvent removed. Purification by column chromatography (hexanes/EtOAc 9/1) gave 2.53 g (62%) of the desired secondary amine as a colorless oil. $^1$H NMR δ1.68 (br.s, 1H), 3.76 (s, 2H), 3.84 (s, 2H), 7.21–7.41 (m, 7H). Arachidonic acid (213 mg, 0.69 mmol) was dissolved in CH$_2$Cl$_2$ (5 mL) and cooled to 0° C. Oxalyl chloride (134 µL, 1.54 mmol) was added dropwise followed by 2 drops of DMF. The ice bath was removed and the mixture stirred at 25° C. for 2 hours. The solvent was evaporated under vacuum. A solution of the acid chloride in CH$_2$Cl$_2$ (3 mL) was added to a solution of amine (1.0 g, 3.49 mmol) in CH$_2$Cl$_2$ (5 mL) at 0° C. The ice bath was removed and the mixture was stirred for two days at 25° C. It was diluted with CH$_2$Cl$_2$ and washed with 5% NaOH and brine. Dried (MgSO$_4$) and removed solvent. The crude product was purified by column chromatography (hexanes/EtOAc 9/1 then 4/1) to give the desired product (O-2247) as a colorless oil (340 mg, 83%) in a 1:1 mixture of rotomers. $^1$H NMR δ0.88 (t, 6H, 6.9 Hz), 1.23–1.41 (m, 12H), 1.79 (q, 4H, 6.9 Hz), 2.01–2.14 (M, 8H), 2.31 (t, 2H, 7.9 Hz), 2.41 (t, 2H, 7.9 Hz), 2.73–2.84 (m, 12H), 4.44 (br.s, 2H), 4.45 (br.s, 2H), 4.54 (br.s, 2H), 4.66 (br.s, 2H), 5.26–5.43 (m, 16H), 7.01–7.42 (m, 14H). Anal. Calcd for $C_{34}H_{42}Cl_3NO \cdot 0.5\ C_2H_4Cl_2 \cdot 0.1\ H_2O$: C, 66.04; H, 7.00. Found: C, 66.05; H, 6.80.

Eicosa-5,8,11,14-tetraenoic acid (4-chloro-benzyl)-(2,4-dichloro-phenyl)amide (O-2248). Used the same procedure as above to synthesize 1.15 g (56%) of the desired amine from 4-chlorobenzaldehyde (1.0 g, 7.11 mmol), 2,4-dichloroaniline (1.27 g, 7.83 mmol), sodium triacetoxyborohydride (2.41 g, 11.38 mmol), acetic acid (0.41 mL, 7.11 mmol) and 1,2-dichloroethane (32 mL). $^1$H NMR δ4.36 (d, 2H, 5.8 Hz), 4.73 (br.s, 1H), 6.46 (d, 1H, 8.5 Hz), 7.03 (dd, 1H, 8.7, 2.2 Hz), 7.22–7.34 (m, 5H). Used the same procedure as above for generating the acid chloride and the subsequent condensation product: used arachidonic acid (234 mg, 0.77 mmol) in CH$_2$Cl$_2$ (5 mL) with oxalyl chloride (147 µL, 1.69 mmol) and DMF (2 drops). The acid chloride in CH$_2$Cl$_2$ (3 mL) was subsequently added to the respective amine (1.1 g, 3.84 mmol) in CH$_2$Cl$_2$ (5 mL). Isolated the desired product (O-2248; 400 mg, 91%) after purification by column chromatography (hexanes/EtOAc 97%/3% then 95%/5%) as a single rotomer. $^1$H NMR δ0.88 (t, 3H, 6.9 Hz), 1.24–1.41 (m, 6H), 1.67 (q, 2H, 7.1 Hz), 1.94–2.05 (m, 6H), 2.75 (m, 6H), 4.03 (d, 1H, 14.3 Hz), 5.22–5.40 (m, 8H), 5.48 (d, 1H, 14.3 Hz), 6.70 (d, 1H, 8.5 Hz), 7.10–7.28 (m, 5H), 7.52 (d, 1H, 2.2 Hz). Anal. Calcd for $C_{33}H_{40}NOCl_3$: C, 69.33; H, 7.06. Found: C, 69.17; H, 7.20.

Example 2

The affinity of O-2093 for the CB$_1$ receptors was measured with the K$_i$ (nM) for the displacement of [$^3$H]CP55940 from whole rat brain membranes as previously described DiMarzo et al., 2002. J. Pharm. Exp. Ther. 300: 984. Efficacy at these as well as other G-protein-coupled receptors was measured as the capability of stimulating the binding of [$^{35}$S]GTP$_\gamma$S to rat hippocampal membranes as previously described DiMarzo et al., 2002. Potency (nM) and efficacy (maximal effect as percentage of the stimulation of the effect of 4 µm capsaicin) at human VR$_1$ receptors were measured as the capability of enhancing [Ca$^{2+}$], via HEK-hVR$_1$ cells as previously described DiMarzo et al., 2002. Data for VR$_1$ and CB$_1$ are means ±S.D. of n=3.

As can be seen in the results presented in Table 1, O-2093 displays very low affinity for CB$_1$, and virtually no affinity for the VR$_1$ receptor. Further tests showed that O-2093 exerts significant inhibition of GTP$_\gamma$S binding which was not sensitive to the CB$_1$ antagonist SR14176A (2 nM, data not shown), nor to the FAAH inhibitor PMSF (50 mM, data not shown).

TABLE 1

Affinity of O-2093 for CB$_1$ and VR$_1$ Receptors

| CB$_1$ affinity (Ki) | GTPgammaS binding (E$_{max}$) | hVR1 potency (EC$_{50}$) |
|---|---|---|
| 1290 ± 140 | −30 (−11.3 to −39.9) | >50,000 (26.9 ± 4.2) |

Example 3

Amelioration of Induced Spasticity

Biozzi ABH mice were injected with 1 mg of mouse spinal cord homogenate emulsified in Freund's complete adjuvant on day 0 and 7 (Baker D. et al 1990. J. Neuroimmunol 28:261). Following 3–4 episodes of paralysis (60–80 days post-inoculation) animals developed spasticity (Baker D. et al 2000. Nature 404:84). This was assessed to detect limb stiffness by analysis using a strain gauge (Baker et al 2000). The analogue signal from the strain gauge was amplified and digitally converted using an ComputerBoards Inc PCM-DAS16S/12 card (Amplicon, Brighton, UK). This was captured using Dacquire V10 software (D.Buckwell, Institute of Neurology, UK) and analyzed using Spike 2 software (Cambridge Electronics Design, UK). The hindlimbs were fully extended twice then moved to full flexion against the strain gauge. The mean of 4–8 individual readings per limb was taken for each time point. Results are expressed as means of forces of resistance to flexion (in Newtons) and SEM per group. Animals were injected with O-2093 dissolved in ethanol (10 mg/ml) and then suspended in intralipid 30% vehicle (Pharmacia, Milton Keynes, UK) and 0.1 ml of compound (0.05 mg/kg) was injected intravenously via the tail vein.

Statistical analysis was performed using Sigmastat 2.0 (Jandel/SPSS, USA) using one-way repeated measures analysis of variance (ANOVA) incorporating a pair-wise Student-Newman-Keuls (SNK) test. The treatments were found to be significantly different (P<0.001) by ANOVA and the SNK test indicated that the observations at 10 min, 30 min and 60 min were significantly different (P<0.001) from levels at baseline. N=13 limbs analyzed from 8 spastic animals. In these animals 3 mice exhibited tremor (2 mice with a limb tremor and one mouse with a head tremor). These were visibly ameliorated within 10 minutes of O-2093 treatment. Likewise 3 mice exhibited evidence of a spastic tail (Baker et al 2000), this was also visibly ameliorated within 10 minutes.

Figure 3A:
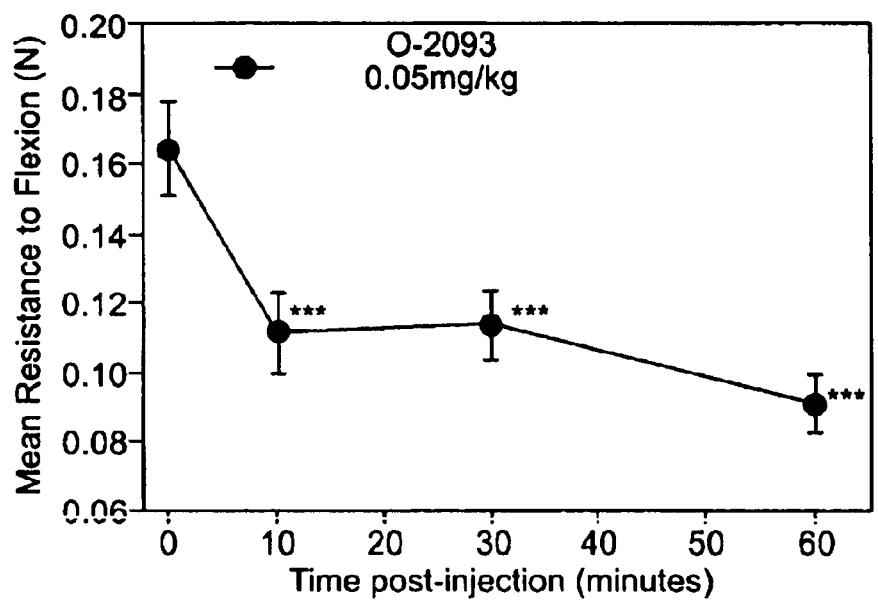
FIGS. 3A and B. A, inhibition of spasticity by administration of O-2093, as measured by mean resistance to flexion. B, inhibition of spasticity by administration of O-2093, as measured by change in resistance to flexion, and in comparison to arvanil and methanandamide.
Figure 3B:
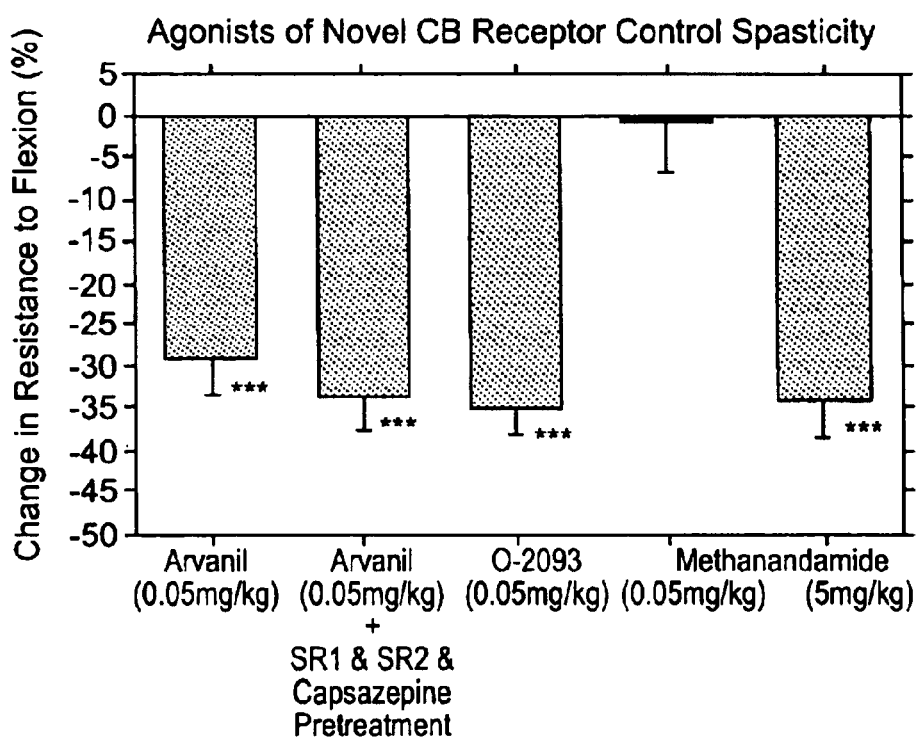
Figure 4A:
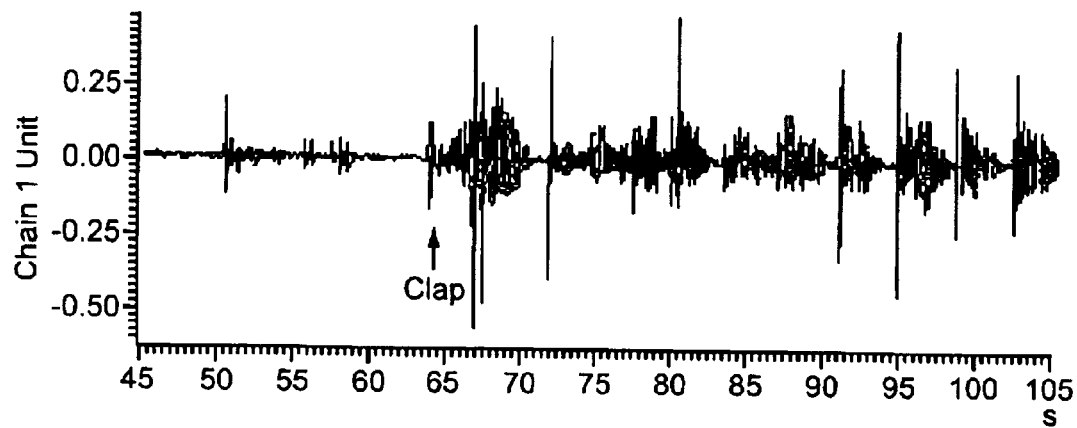
FIGS. 4A and B. Body tremor in a spastic mutant mouse before and after treatment with O-2093. A, response to hand clap prior to treatment. B, response to hand clap after treatment.
Figure 4B:
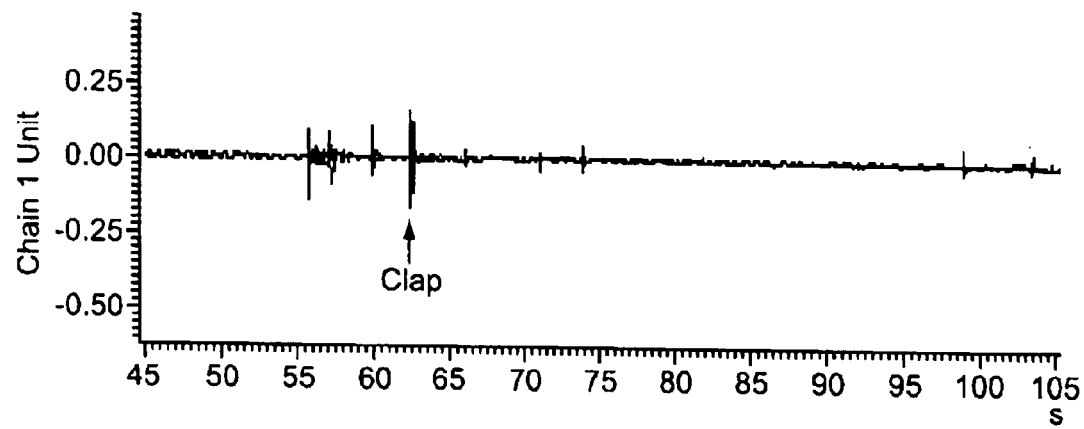

In some instances, the percentage difference between baseline (0 min) and that observed 30 minutes after treatment with O-2093 were analyzed and compared to treatment with arvanil and methanandamide, both of which are known to bind CB1 receptors. Arvanil also binds to the vanilloid receptor (VR-1). Arvanil treatment was carried out with and without pretreatment of the animals with SR141617A, SR144528 (known to inhibit CB1 and CB2 receptor function, respectively) and capsazepine, a known antagonist of the vanilloid recpetor (VR-1). The mean and standard error of the mean (SEM) were ascertained following injection of: O-2093 (0.05 mg/kg O-2093); arvanil (Cayman Chem. 0.05 mg/kg); or arvanil in animals that had been pretreated (−20 min with 5 mg/kg i.v. SR141617A, SR144528 (NIDA, USA) and 40 mg/kg capsazepine); and 0.05 mg/kg or 5 mg/kg of methanandamide. The results are given in FIGS. 3A and B. As can be seen, FIG. 3A shows that mean resistance to flexion decreased significantly after injection of O-2093. FIG. 4B shows that administration of O-2093 results in an approximate 35% decrease in resistance to flexion. This is in comparison to results obtained with arvanil and methanandamide.

This example demonstrates that O-2093 exhibits an antispastic effect in an experimental model that mimics multiple sclerosis.

Example 4

Amelioration of Tremor in Spastic Mouse Model

The mutant Spastic (Glycine Receptor beta Subunit Glrb$^{spa/spa}$) mouse (model of stiff baby syndrome) on a C57BL/6 background has a mutation in the glycine receptor beta subunit (Glrb) resulting a reduction in functional glycine receptors in the adult mouse. These mice develop limb tremors and episodes of rapid tremor and rigidity of the limb and trunk muscles. This is often triggered by sudden disturbances (Chai C. K. 1961 J. *Heredity* 52:241). The body tremor was assessed following attachment of a lightweight unidirectional accelerometer (Entrain, UK) mounted on the base of the tail. The Spike 2 trace was measured before and after (10 min) i.v. injection of O-2093 (0.05 mg/kg) The results are given in FIGS. 4A (before O-2093 administration) and 4B (after O-2093 administration).

As can be seen, the administration of O-2093 significantly ameliorated the tremor developing from the "startle" response induced by a hand clap.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A compound having the structural formula

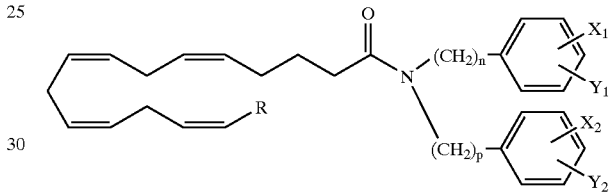

wherein n ranges from 0 to 5, p ranges from 0 to 5, and n and p may be the same or different;

$X_1$=H, alkyl, Cl, Br, I, F, OH, or O-alkyl; $X_2$=H, alkyl, Cl, Br, I, F, OH, or O-alkyl; $Y_1$=H, alkyl, Cl, Br, I, F, OH, or O-alkyl; $Y_2$=H, alkyl Cl, Br, I, F, OH, or O-alkyl; and $X_1$, $X_2$, $Y_1$ and $Y_2$ can be the same or different; and

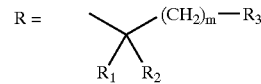

wherein m ranges from 1–7;

$R_1$=$R_2$=H, or alkyl; and $R_3$=OH, Cl, Br, I, CN, ONO, $ONO_2$, $NO_2$, H, or $CH_3$.

2. The compound of claim 1 wherein $X_1$ and $X_2$ are Cl; $Y_1$ and $Y_2$ are OH; n and p are 1; $R_1$ and $R_2$ are H; m=3 and $R_3$=$CH_3$.

3. The compound of claim 1 wherein $X_1$ is H and $X_2$ is Cl; $Y_1$ and $Y_2$ are Cl; n and p are 1; $R_1$ and $R_2$ are H; m=3 and $R_3$=$CH_3$.

4. The compound of claim 1 wherein $X_1$ is H and $X_2$ is Cl; $Y_1$ and $Y_2$ are Cl; n is 1 and p is 0; $R_1$ and $R_2$ are H; m=3 and $R_3$=$CH_3$.

5. A method of treating motor disorders in a patient in need thereof, comprising the step of administering to said patient a sufficient amount of a pure or salt form of a compound having the structural formula

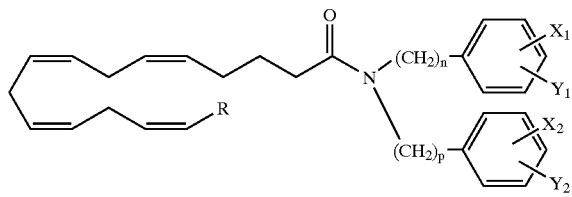

wherein
  n ranges from 0 to 5, p ranges from 0 to 5, and n and p may be the same or different;
  $X_1$=H, alkyl, Cl, Br, I, F, OH, or O-alkyl; $X_2$=H, alkyl, Cl, Br, I, F, OH, or O-alkyl; $Y_1$=H, alkyl, Cl, Br, I, F, OH, or O-alkyl; $Y_2$=H, alkyl, Cl, Br, I, F, OH, or O-alkyl; and $X_1$, $X_2$, $Y_1$ and $Y_2$ can be the same or different; and

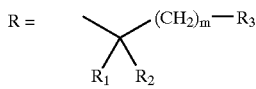

wherein
  m ranges from 1–7;
  $R_1$=$R_2$=H, or alkyl; and
  $R_3$=OH, Cl, Br, I, CN, ONO, $ONO_2$, $NO_2$, H, or $CH_3$.

6. The method of claim 5 wherein $X_1$ and $X_2$ are Cl; $Y_1$ and $Y_2$ are OH; n and p are 1; $R_1$ and $R_2$ are H; m=3 and $R_3$=$CH_3$.

7. The method of claim 5 wherein $X_1$ is H and $X_2$ is Cl; $Y_1$ and $Y_2$ are Cl; n and p are 1; $R_1$ and $R_2$ are H; m=3 and $R_3$=$CH_3$.

8. The method of claim 5 wherein $X_1$ is H and $X_2$ is Cl; $Y_1$ and $Y_2$ are Cl; n is 1 and p is 0; $R_1$ and $R_2$ are H; m=3 and $R_3$=$CH_3$.

9. The method of claim 5 wherein said step of administering is carried out by an administration means selected from the group consisting of intraperitoneal, subcutaneous, orally, intramuscularly, and intravenously.

10. The method of claim 5 wherein said motor disorder results from a disorder selected from the group consisting of multiple sclerosis, spinal cord injury, Huntington's disease and Parkinson's disease.

11. The method of claim 5 wherein said motor disorder is selected from the group consisting of spasticity, gait abnormality, and ataxia.

12. A method for the treatment of spasticity in a patient in need thereof, comprising the step of
  administering to said patient a sufficient amount of a compound having the structural formula

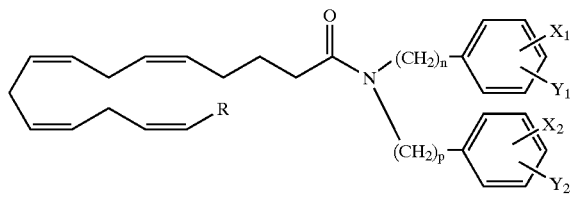

wherein
  n ranges from 0 to 5, p ranges from 0 to 5, and n and p may be the same or different; $X_1$=H, alkyl, Cl, Br, I, F, OH, or O-alkyl; $X_2$=H, alkyl, Cl, Br, I, F, OH, or O-alkyl; $Y_1$=H, alkyl, Cl, Br, I, F, OH, or O-alkyl; $Y_2$=H, alkyl, Cl, Br, I, F, OH, or O-alkyl; and $X_1$, $X_2$, $Y_1$ and $Y_2$ can be the same or different; and

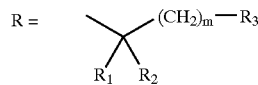

wherein
  m ranges from 1–7;
  $R_1$=$R_2$=H or alkyl; and
  $R_3$=OH, Cl, Br, I, CN, ONO, $ONO_2$, $NO_2$, H, or $CH_3$.

13. The method of claim 12 wherein $X_1$ and $X_2$ are Cl; $Y_1$ and $Y_2$ are OH; n and p are 1; $R_1$ and $R_2$ are H; m=3 and $R_3$=$CH_3$.

14. The method of claim 12 wherein $X_1$ is H and $X_2$ is Cl; $Y_1$ and $Y_2$ are Cl; n and p are 1; $R_1$ and $R_2$ are H; m=3 and $R_3$=$CH_3$.

15. The method of claim 12 wherein $X_1$ is H and $X_2$ is Cl; $Y_1$ and $Y_2$ are Cl; n is 1 and p is 0; $R_1$ and $R_2$ are H; m=3 and $R_3$=$CH_3$.

16. The method of claim 12 wherein said step of administering is carried out by an administration means selected from the group consisting of intraperitoneal, subcutaneous, orally intramuscularly, and intravenously.

17. A composition comprising,

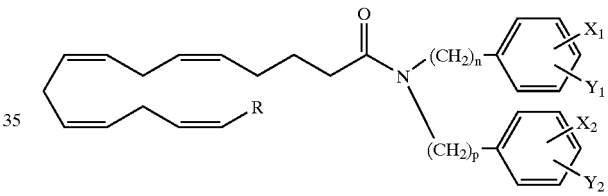

wherein
  n ranges from 0 to 5, p ranges from 0 to 5, and n and p may be the same or different;
  $X_1$=H, alkyl, Cl, Br, I, F, OH, or O-alkyl; $X_2$=H, alkyl, Cl, Br, I, F, OH, or O-alkyl; $Y_1$=H, alkyl, Cl, Br, I, F, OH, or O-alkyl; $Y_2$=H, alkyl, Cl, Br, I, F, OH, or O-alkyl; and $X_1$, $X_2$, $Y_1$ and $Y_2$ can be the same or different; and wherein
  m ranges from 1–7;
  $R_1$=$R_2$=H or alkyl; and
  $R_3$=OH, Cl, Br, I, CN, ONO, $ONO_2$, $NO_2$, H, or $CH_3$; and a carrier, said compound being dissolved or dispersed in said carrier.

18. The composition of claim 17 wherein said compound is present in said carrier in salt form.

* * * * *

UNITED STATES PATENT AND TRADEMARK OFFICE
CERTIFICATE OF CORRECTION

| | | |
|---|---|---|
| PATENT NO. | : 6,800,770 B2 | Page 1 of 1 |
| APPLICATION NO. | : 10/346164 | |
| DATED | : October 5, 2004 | |
| INVENTOR(S) | : Billy Martin et al. | |

It is certified that error appears in the above-identified patent and that said Letters Patent is hereby corrected as shown below:

In the Specification

At Column 1, please delete lines 14-18 and insert the following:

--STATEMENT OF GOVERNMENT INTEREST

This invention was made with government support under contract numbers DA09789 and DA08904 awarded by the National Institutes of Health. The government has certain rights in the invention.--

Signed and Sealed this
Thirtieth Day of December, 2014

Michelle K. Lee
*Deputy Director of the United States Patent and Trademark Office*